United States Patent [19]

Baker

[11] Patent Number: 4,553,271
[45] Date of Patent: Nov. 19, 1985

[54] ARTIFICIAL SPHINCTER APPARATUS AND METHOD

[75] Inventor: Charles D. Baker, Lehi, Utah

[73] Assignee: University of Utah Research Institute, Salt Lake City, Utah

[21] Appl. No.: 367,533

[22] Filed: Apr. 12, 1982

Related U.S. Application Data

[63] Continuation-in-part of Ser. No. 194,528, Oct. 6, 1980, abandoned.

[51] Int. Cl.[4] ................................................. A61F 1/00
[52] U.S. Cl. ..................................... 623/14; 128/1 R; 128/346
[58] Field of Search ............... 128/DIG. 25, 346, 325, 128/326, 1 R, 303 R; 3/1; 74/142; 138/45

[56] References Cited

U.S. PATENT DOCUMENTS

| | | | |
|---|---|---|---|
| 427,014 | 4/1890 | Roberts | 74/142 |
| 536,469 | 3/1895 | Hathaway et al. | 74/142 |
| 1,849,971 | 3/1932 | Baughan | 74/142 |
| 2,434,835 | 5/1946 | Colley | 138/45 |
| 2,530,961 | 7/1947 | Hansen | 74/142 |
| 2,569,850 | 10/1951 | Falconer | 138/45 |
| 3,705,580 | 12/1972 | Gauthier | 128/DIG. 25 |
| 4,092,010 | 5/1978 | Carlson | 138/45 |
| 4,178,915 | 12/1979 | Szinicz et al. | 128/DIG. 25 |
| 4,194,848 | 3/1980 | Kingsford | 138/45 |

*Primary Examiner*—Richard J. Apley
*Assistant Examiner*—Gregory Beaucage
*Attorney, Agent, or Firm*—Workman, Nydegger & Jensen

[57] ABSTRACT

An artificial sphincter apparatus and method, the artificial sphincter including a pair of parallel, coaxially mounted rings with at least one ring rotatable relative to the other ring. A plurality of tie members mounted circumferentially to the rings extend between the rings and are angularly moved relative to the axis of the artificial sphincter upon relative rotation between the rings so as to selectively occlude or open a bowel engaged by the artificial sphincter. An actuator mechanism mounted on the artificial sphincter permits the artificial sphincter to be operated externally even when the artificial sphincter is implanted.

15 Claims, 7 Drawing Figures

ARTIFICIAL SPHINCTER APPARATUS AND METHOD

RELATED APPLICATIONS

This application is a continuation-in-part application of my copending application for Constriction Apparatus and Method, Ser. No. 194,528, filed Oct. 6, 1980, now abandoned.

BACKGROUND

1. Field of the Invention

This invention relates to a constriction apparatus and, more particularly, to a constriction apparatus and method particularly adapted to an artifical sphincter wherein the apparatus includes a pair of spaced, parallel, coaxial rings, at least one ring being rotatable, the rings having a plurality of tie members arrayed annularly between the rings so that relative rotation between the rings causes the tie members to move inwardly in a constricting movement toward the axis of the constriction apparatus.

2. The Prior Art In the field of medicine and also medical research, it is frequently necessary to clamp a vessel or otherwise stop the flow of fluid such as blood flow through a vessel. Vascular clamps are well known and generally involve two jaw members which transversely clamp the vessel to shut off the flow of blood. However, it is also well known that vessels such as blood vessels, and the like, have irregular wall thicknesses with corresponding irregularities in the inner wall surface so that a clamp having jaws which move in a parallel clamping action must clamp the vessel tight enough to seal the thinnest portion of the irregular wall surface. Otherwise, there will be leakage past the clamp. Accordingly, the conventional vascular clamp, if used for a significant period of time, results in pressure necrosis of the underlying vascular tissue. While many procedures have been adapted to alleviate this particular problem, it is believed that it would be a significant advancement in the art to provide a novel constriction apparatus and method for gently constricting flow of fluid through a vessel with minimal damage to the vessel through pressure necrosis. Numerous other applications require a constricting-type movement such as encountered in a sphincter-type muscle arrangement wherein the muscular movement contracts towards the axis of the muscular structure. Various other flow control devices could also benefit from an axially oriented constricting movement.

A constriction or crimping apparatus is disclosed by Falconer (U.S. Pat. No. 2,569,850) and includes a plurality of rods mounted circumferentially around an axial opening. A tubing is inserted in the opening and is crimped by twisting the rods about the axis. The basic principle shown by the patent is analogous to the mechanism of the aritifical sphincter apparatus and method of the present invention.

Other constricting devices are shown in the patents of Colley (U.S. Pat. No. 2,434,835); Carlson, Jr. (U.S. Pat. No. 4,092,010); and Kingsford (U.S. Pat. No. 4,194,848). However, these devices use entirely different operative mechanisms from that of the present invention.

It would, therefore, be an advancement in the art to provide a novel constriction apparatus which would provide the basic principle for a sphincter-type orifice muscle for various applications. Such a novel apparatus and method is disclosed and claimed herein.

BRIEF SUMMARY AND OBJECTS OF THE INVENTION

The present invention relates to a novel constriction apparatus and method, the apparatus including two, parallel and axially mounted rings interconnected by a plurality of annularly arrayed tie members extending between the two rings. Relative rotation between the rings causes the tie members to be angularly and tangentially brought toward the axis of the constriction apparatus. The type and length of the tie members and, correspondingly, the spatial separation of the ring members as well as the diameter of the ring members determines the characteristics of the constricting force imparted by the constriction apparatus.

It is, therefore, a primary object of this invention to provide a novel constriction apparatus.

Another object of this invention is to provide an improved method for imparting a constricting force to an object.

Another object of this invention is to provide a constriction apparatus wherein the type or nature of the constricting force may be selectively predetermined by the choice of ring diameter, tie member length, or spatial separation of the ring members as well as the flexibility of the individual tie members.

Another object of this invention is to provide a novel constriction apparatus wherein the area of constriction may be selectively predetermined by selectively predetermining the diameter and spatial separation of the two ring members.

Another object of this invention is to provide an artificial sphincter having the operative mechanism incorporated into the structure.

Another object of this invention is to provide an artificial sphincter enclosed in a fluid impervious membrane, the operative mechanism being activated through the membranes.

These and other objects and features of the present invention will become more fully apparent from the following description and appended claims taken in conjunction with the accompanying drawing.

DETAILED DESCRIPTION OF THE PREFERRED EMBODIMENTS

Figure 1:
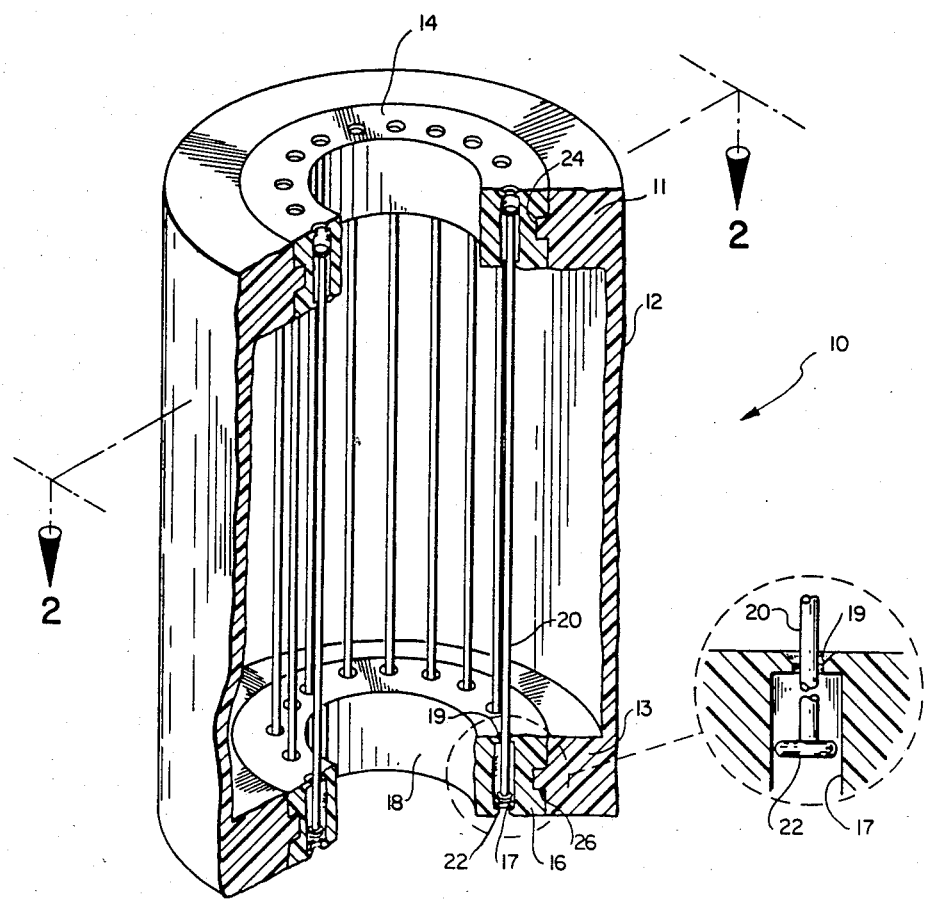
FIG. 1 is a perspective view of a first preferred embodiment of the constriction apparatus of this invention with a portion broken away and an enlarged view to reveal internal construction.

The invention is best understood by reference to the drawing wherein like parts are designated with like numerals throughout.

Referring now more particularly to FIG. 1, a first preferred embodiment of the novel constriction apparatus of this invention is shown generally at 10 and includes a hollow support column 12 configurated as a right cylinder and rotatably supporting a pair of spaced, coaxial ring members 14 and 16 in parallel relationship. Mounts 11 and 13 at each end of support column 12 rotatably support ring members 14 and 16, respectively, and hold the same therein in their respective relationships with mating, circular bearings 24 and 26, respectively. Circular bearings 24 and 26 are shown herein as constituting an annular undercut in the respective ring members 14 and 16 cooperating with an internal shelf on the respective mounts 11 and 13. Clearly, however, circular bearings 24 and 26 may be of any suitable configuration to provide the appropriate frictional and support relationship between the respective ring member 14 and 16 and its corresponding mount 11 and 13.

Figure 2:
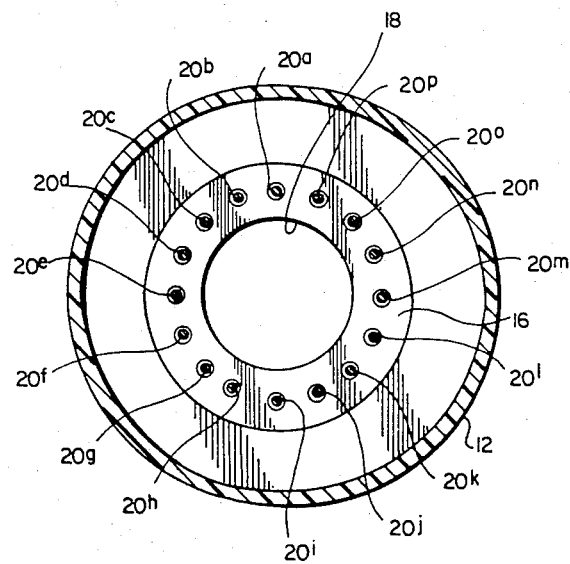
FIG. 2 is a cross-section taken along lines 2—2 of FIG. 1.
Figure 3:
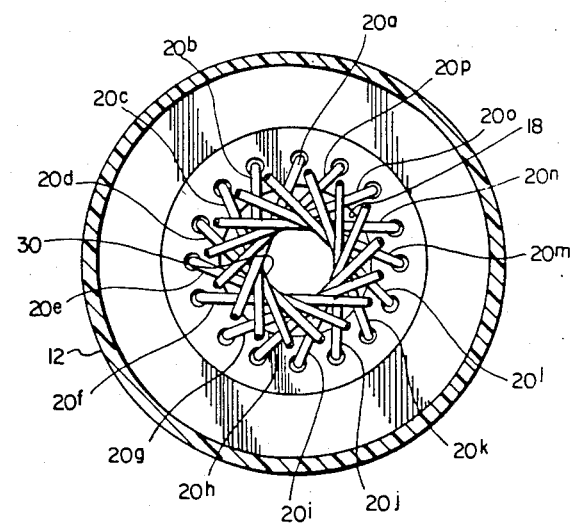
FIG. 3 is the cross-sectional view of FIG. 2 showing a relative rotation of the rings to illustrate the orientation and constricting movement of the tie members thus obtained.

Rings 14 and 16 are coaxial and form a throughbore 18 through which an object (not shown) to be constricted may be placed and constricted by the inward movement of the members 20 as will be discussed more fully hereinafter. Tie members 20 are shown as semirigid rods in this illustrated embodiment. However, tie members 20 can be fabricated from any suitable material to incorporate the desired characteristics into constriction apparatus 10. For example, tie members 20 may be fabricated from a flexible material or even an elastic material. Tie members 20 are mounted at each end in ring members 14 and 16 in a limited, slideable and rotatable relationship. With respect to the enlarged view of a portion of FIG. 1, the end of a tie member 20 is shown extending through a countersunk throughbore 19 into a bore 17. A head 22 prevents tie member 20 from being pulled through countersunk throughbore 19. The length of bore 17 is selectively predetermined so that there is sufficient longitudinal movement of tie members 20 relative to ring members 14 and 16 to accommodate the relative movement of the ends of tie members 20 when ring members 14 and 16 are rotated relative to each other. For example, and with particular reference to FIGS. 2 and 3, a plurality of tie members 20a–20p are shown mounted in ring member 16 in an annular array around throughbore 18. With particular reference to FIG. 3, the view shown is as though ring member 14 (FIG. 1) has been rotated counterclockwise, causing each of tie members 20a–20p to be moved angularly from a position perpendicular to the plane of the drawing to an angle relative to the axis of constriction apparatus 10 while simultaneously bringing the members 20a–20p together in a constricting movement toward the center of throughbore 18. If viewed from the side, the tie members exhibit a profile generally corresponding to a pair of end-to-end cones having a generally frustoconical configuration with the area of constriction at the center of tie members 20a–20p being selectively predetermined by several factors including, for example, (a) the length of the tie members 20a–20p relative to (b) the diameter of ring members 14 and 16 and, more particularly, the diameter of the annular array of tie members 20a–20p on ring members 14 and 16, and in relationship also with (c) the length of support column 12 and, more particularly, the spatial separation of ring members 14 and 16.

An additional factor affecting the length of the constriction surface relates to the flexibility or "softness" of tie members 20a–20p. For example, tie members 20a–20p shown herein are illustrated as essentially semirigid rods so that the constriction movement of tie members 20a–20p toward the axis of constriction apparatus 10 will be generally limited to a theoretical maximum of a 180° relative rotation between ring member 14 and ring member 16. However, the theoretical maximum of 180° will not be achieved due to the individual diameters of each of tie members 20a–20p and the relative stiffness thereof inhibiting tie members 20a–20p to a constriction wherein the sides of tie members 20a–20p are in contact at the axis of constriction apparatus 10. Ring members 14 and 16 have been rotated through a relative rotation somewhat less than 180°. However, as can be clearly seen from the description of the drawing of the novel constriction apparatus of this invention, tie members 20a–20p could be selectively fabricated from a suitable, flexible or otherwise "soft" material or even elastic having a predetermined degree of elasticity to thereby accommodate relative rotation through more than 180° between ring member 14 with respect to ring member 16 with a corresponding spiral twisting of tie members 20a–20p relative to each other. The foregoing axially lengthens the area of constriction of tie members 20a–20p when included with the previous considerations with respect to the area of constriction.

Figure 4:
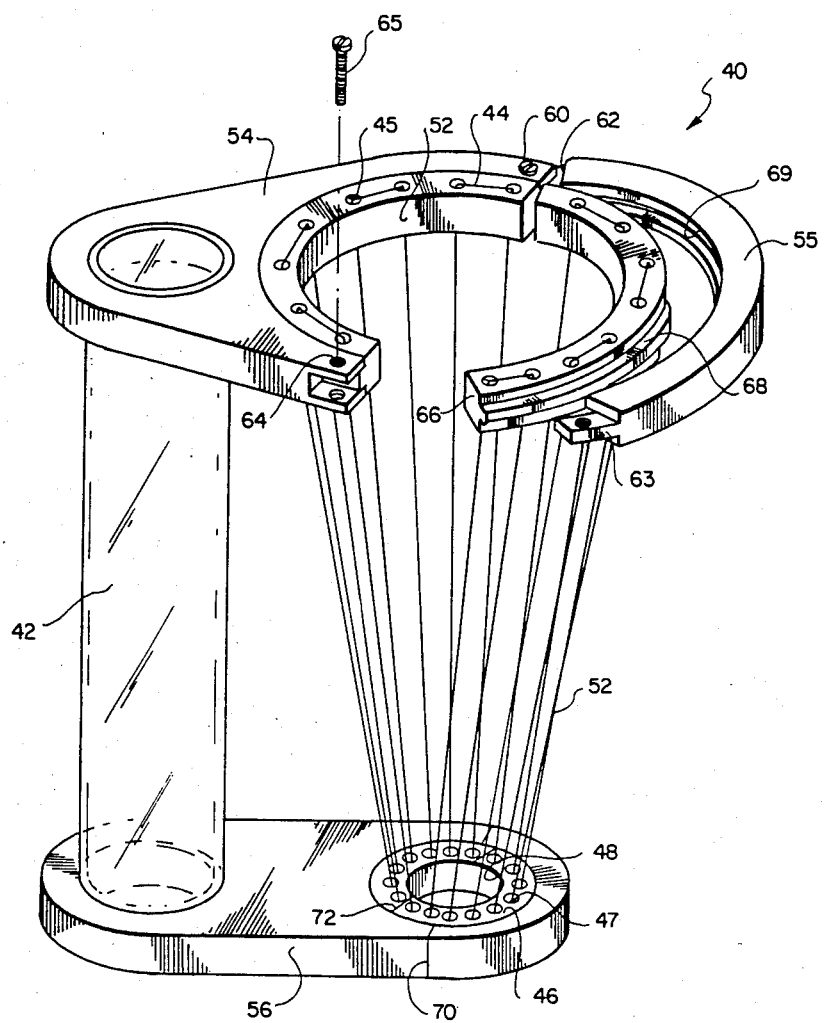
FIG. 4 is a perspective view of a second preferred embodiment of the novel constriction apparatus of this invention.

Referring now more particularly to FIG. 4, a second preferred embodiment of the novel constriction apparatus of this invention is shown generally at 40 and includes an upper ring member 44 supported in a mount 54 parallel and coaxial to a corresponding, lower ring member 46 supported in a mount 56. Mounts 54 and 56 are rigidly supported in parallel relationship by an offset, support column 42. Upper ring member 44 is interconnected to lower ring member 46 by a plurality of tie members 50.

Tie members 50 are configured as a plurality of cords interwoven through a plurality of throughbores 45 in the upper, enlarged ring member 44 and a plurality of corresponding throughbores 47 in the lower, smaller ring member 46. Tie members 50 thereby form a conical throughbore through constriction apparatus 40. Each of ring members 44 and 46 are also configurated as split ring members and each are operable to be opened along a joinder 66 for ring member 44 and joinder 72 for ring member 46. With particular reference to ring member 44, ring member 44 is configurated as a split ring retained by a tongue 68 in a groove 69 of the surrounding mount 55. Mount 55 is hinged at hinge point 60 and adapted to be interconnected through a bolt 65 joining a tongue 63 to a corresponding bracket 64. A similar joint for mount 56 is illustrated schematically as joint 70.

The configuration of ring members 44 and 46 is such to accommodate opening of the ring members at joinders 66 and 72, respectively, to thereby encircle an object (not shown) with constriction apparatus 40. Thereafter, the split ring members may be closed, interlocked in the respective mounts and rotated relative to each other to thereby impart a constricting force to the object (not shown) thus engaged. However, as discussed hereinbefore and as shown in the construction apparatus 40, the point of constriction will be nearer ring member 46 by reason of the relative diameters of ring members 44 and 46. While the relative sizes of ring members 44 and 46 may be somewhat exaggerated herein, the principle is clearly illustrated to show the relative difference between openings 52 and 48 of ring members 44 and 46, respectively.

While support member 42 is shown as an external support apparatus, either of constriction apparatus 10 (FIG. 1) and constriction apparatus 40 (FIG. 4) could be selectively interchanged with respect to support members 12 (FIG. 1) and support member 42 (FIG. 4) to thereby place the constricting apparatus of this invention either internally or externally of the particular support system. In either configuration, the relative distance of the respective ring members is maintained so as to impart the desired constricting forces to the object (not shown) encircled thereby.

Figure 5:
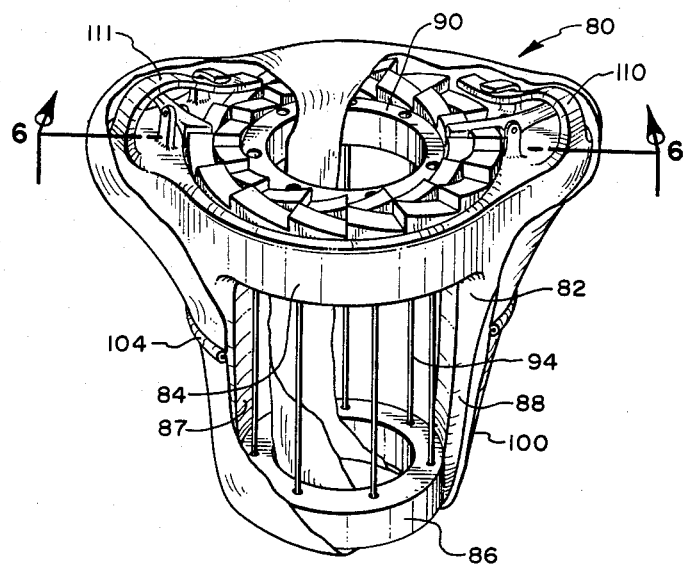
FIG. 5 is a perspective view of an artificial sphincter incorporating the novel apparatus of this invention, portions being broken away to reveal internal construction.
Figure 6:
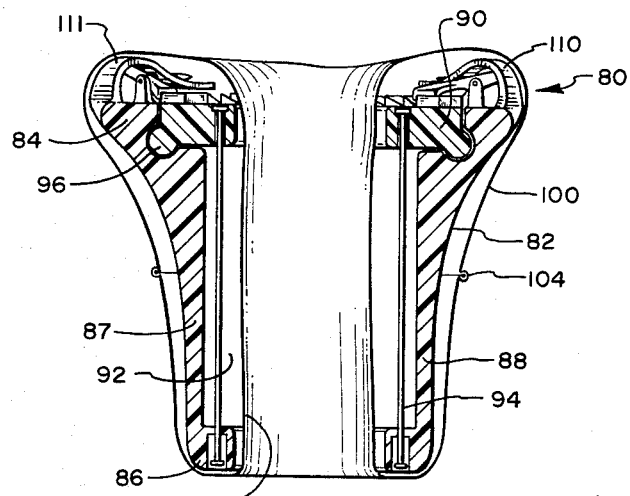
FIG. 6 is a cross-sectional view taken along lines 6—6 of FIG. 5.
Figure 7:
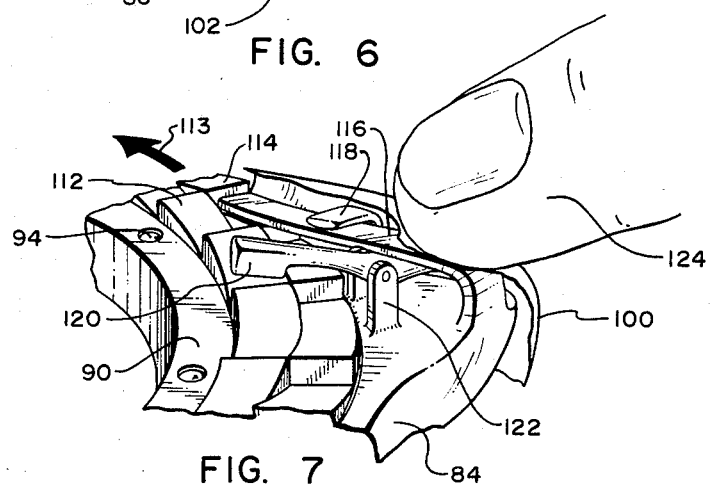
FIG. 7 is a fragmentary enlargement of a portion of FIG. 5 and showing a portion of a finger in order to demonstrate operation of the artificial sphincter.

Referring now more particularly to FIGS. 5–7, the constriction apparatus of this invention is shown configurated into an artificial sphincter 80. Artificial sphincter 80 is constructed with a basal framework 82 having an upper ring support 84 mounted to a lower ring 86 by a pair of support columns 87 and 88. Lower ring 86 is stationary while upper ring support 84 has rotatably mounted therein an upper ring 90, upper ring 90 being rotatable in a plane parallel to lower ring 86 so as to provide the desired relative rotation between upper ring 90 and lower ring 86. A plurality of tie members 94 are mounted circumferentially to each of upper ring 80 and lower ring 86 to thereby create an iris-like constrictive action of a lumen or throughbore 92 as discussed hereinbefore with respect to the embodiments shown in FIGS. 1–4. Upper ring 90 also includes an annular detent 96 which cooperates in a corresponding, annular groove in upper ring support 84. The dimensions and materials of construction of upper ring 90 and upper ring support 84 are such that detent 96 is held in a snap-fit relationship in upper ring support 84.

Since artificial sphincter 80 is intended for implantation, all of the materials of construction intended to be in contact with living tissue are fabricated from readily available, biocompatible, plastic materials. Alternatively and preferentially, the entire artificial sphincter apparatus 80 is enclosed in a fluid-impervious, flexible, bicompatible membrane 100. Membrane 100 is configurated as a generally tubular member having a diametrically reduced waist adapted to reside within and form a lumen 102 through the hollow throughbore 92 of artificial sphincter 80. The ends of the tubular member are diametrally enlarged and have matching diameters so that each end may be folded outwardly over the respective end of artificial sphincter 80 and brought together in a joinder 104 circumferentially around the exterior of artificial sphincter 80. By this technique, artificial sphincter 80 is completely isolated within the envelope of membrane 100. Rotation of upper ring 90 causes tie members 94 to constrict lumen 102 and correspondingly, a section of bowel or the like (not shown) passing therethrough. Advantageously, since tie members 94 are moved inwardly in an iris-like constrictive action similar to that shown in FIG. 3, there is very little, if any, twisting motion imparted to lumen 102 by such action.

Rotation of upper ring 90 is accomplished by movement of actuator mechanisms 110 and 111 on each side of artificial sphincter 80. Since the operation of actuator mechanisms 110 and 111 is identical with the exception of the direction of rotation of upper ring 90, only the operation of the right-hand side of actuator mechanisms 110 will be discussed. Attention is particularly directed to FIG. 7 wherein actuator mechanism 110 is shown greatly enlarged for ease of presenting detail and described the operation thereof. Upper ring 90 not only forms a support for tie members 94, the ends of two of which can be seen in FIG. 7, but also includes an inner rachet 112 and an outer rachet 114. Actuation of actuator mechanism 111 cooperates with inner rachet 112 to rotate upper ring 90 in a clockwise direction while actuator mechanism 110 cooperates with outer rachet 114 to rotate upper ring 90 in a counterclockwise direction, as shown schematically by arrow 113.

Actuator mechanism 110 includes a resilient arm 116 formed as an integral part of upper ring support 84 and held in a position above but generally parallel to the respective rachet, in this case, outer rachet 114, by a stop 118. Stop 118 and the resilience and length of arm 116 are selectively configured so as to hold the end of arm 116 above the outer rachet 114 until arm 116 is depressed, as shown in FIG. 7. In particular, a finger 124 pressing against the resiliency of arm 116 causes arm 116 to extend underneath stop 118 so that the end of arm 116 engages a detent in outer rachet 114, causing upper ring 90 to be rotated in a counterclockwise direction, indicated by arrow 113. A dog 120 acts as a detent in cooperation with inner rachet 112 to prevent counterclockwise movement of upper ring 90 whenever actuator mechanism 110 is not in operation. Dog 120 is pivotally mounted to a pivot extending upwardly from upper ring support 84 and extends beneath arm 116. When arm 116 is depressed by finger 124, dog 120 is raised, thereby permitting upper ring 90 to be rotated in the aforedescribed counterclockwise direction, arrow 113. A corresponding dog, pivot, resilient arm is found in actuator mechanism 111 to cause clockwise rotation of upper ring 90. When upper ring 90 is rotated in a clockwise direction by actuator mechanism 111, dog 120 is raised by the ramp-like surface of inner rachet 112 and then dropped into the next succeeding detent. Accordingly, the operator (not shown) can selectively operate the constrictive action of artificial sphincter 80 so as to either open or close a bowel (not shown) passing through lumen 102. Furthermore, since artifical sphincter 80 is specifically configured to be implanted in a body with actuator mechanisms 110 and 111 beneath the outer skin surface, the operator (not shown) can selectively open or close artificial sphincter 80 as desired.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An artificial sphincter comprising:
   a first ring member and a second ring member rotatably mounted parallel and coaxially with the first ring member and at a predetermined distance from the first ring member;
   support means for supporting the first ring member relative to the second ring member;
   a plurality of tie members extending between the first ring member and the second ring member so that relative rotation between the ring members causes the tie members to constrict inwardly toward the axis of the first ring member and the second ring member;

actuator means for rotating at least the first ring member relative to the second member; and a flexible, fluid-impervious membrane means enclosing the artificial sphincter.

2. The artificial sphincter defined in claim 1 wherein the first ring member and the second ring member each comprise split ring means for opening the first ring member and the second ring member and to encompass an object with the first ring member encircling the object at a first position and the second ring member encircling the object at a second position so that rotation of the second ring member relative to the first ring member causes said tie members to impart a constrictive movement against the object.

3. The artificial sphincter defined in claim 1 wherein the first ring member is configured with a first diameter and the second ring member is configured with a second diameter.

4. The artificial sphincter defined in claim 1 wherein the support means comprises an annularly arrayed support apparatus disposed about the axis of the first ring member and the second ring member.

5. The artificial sphincter defined in claim 1 wherein the support means comprises a support column offset from the axis of the first ring member and the second ring member.

6. The artificial sphincter defined in claim 1 wherein the tie members comprise a plurality of rods.

7. The artificial sphincter defined in claim 1 wherein the tie members comprise a plurality of cord means.

8. The artificial sphincter defined in claim 1 wherein the actuator means comprises detent means circumscribing the first ring member and actuator arm means operating in cooperating relationship with the detent means.

9. The artificial sphincter defined in claim 8 wherein the actuator arm means comprises a resilient arm and a stop, the resilient arm being curved outwardly from the plane of the first ring member and cooperating with the stop so that as the resilient arm is depressed toward the first ring member, the stop directs the arm into engagement with the detent means to turn the first ring member.

10. The artificial sphincter defined in claim 9 wherein the actuator arm means further comprises a dog for the detent means, the dog cooperating with the resilient arm to release the dog from the detent means when the resilient arm is depressed into contact with the detent means.

11. The artificial sphincter defined in claim 1 wherein the membrane means comprises a tubular element flaring outwardly at each end to a corresponding diameter so as to accomodate being inserted through the artificial sphincter and each end being folded toward each other and sealingly joined along the diameter.

12. An artificial sphincter comprising:
a first split ring member;
a second split ring member;
support means for rotatably mounting the first split ring member coaxially with and parallel to the second split ring member at a fixed, predetermined distance;
a plurality of tie members extending between the first split ring member and the second ring member so that rotation of the first split ring member relative to the second split ring member causes a generally transverse movement of the tie members relative to the axis of the artificial sphincter;
actuator means for rotating the first split ring member; and
a fluid-impervious envelope for the artificial sphincter.

13. A method for constricting a bowel comprising:
mounting a first ring member at a first position around the object and a second ring member at a second position around the object and spaced from the first position a predetermined distance, the second ring member being parallel and coaxial about a common axis with the first ring member;
interconnecting a plurality of tie members annularly between the first ring member and the second ring member; and
constricting the bowel by rotating the first ring member relative to the second ring member while maintaining the predetermined distance between the first ring member and the second ring member thereby causing the tie members to be brought laterally toward the axis of the first ring member and the second ring member, the lateral movement of the tie members causing said constriction.

14. The method defined in claim 13 wherein the mounting step comprises encircling the bowel with the first ring member, the second ring member and the tie members so that the constricting step includes imparting a constrictive force to the bowel.

15. An intestinal control valve for surrounding the anal-terminating descending intestine of a patient for realizing continence, said valve including in combination:
(a) an upper stationary ring;
(b) a lower rotatable ring in an axially aligned position with said stationary ring;
(c) a plurality of rods extending from said lower rotatable ring through aligned openings in said upper stationary ring in directions parallel to and spaced a given radial distance from the axis of the rings when the rotatable ring is in a first position; and
(d) a toroidal member having an inner flexible part extending between the rings surrounding the anal-terminating descending intestine with the rods passing externally of the flexible part and an outer rigid part passing externally around the rings and rods whereby rotation of said rotatable ring within said toroidal member through a given angle to a second position twists the rods to decrease the given radial distance of the centers of the rods from the axis of the rings to thereby radially contract and flexible part to controllably reduce the passage through the anal-terminating descending intestine.

* * * * *

UNITED STATES PATENT AND TRADEMARK OFFICE
CERTIFICATE OF CORRECTION

PATENT NO. : 4,553,271

DATED : November 19, 1985

INVENTOR(S) : Charles D. Baker

It is certified that error appears in the above-identified patent and that said Letters Patent is hereby corrected as shown below:

```
Column 1, line 24, begin a new paragraph with the word "In"
Column 3, line 28, "the members" should be --tie members--
Column 3, line 56, "the members" should be --tie members--
Column 4, line 51, "44. ring" should be --44, ring--
Column 5, line 28, "ring 80" should be --ring 90--
Column 5, line 44, "bicompatible" should be
--biocompatible--
Column 5, lines 45-46, "diametrically" should be
-diametrally--
Column 5, line 68, "mechanisms" should be --mechanism--
Column 8, line 60, "and flexible" should be --said
flexible--
```

Signed and Sealed this

Twenty-fifth Day of February 1986

[SEAL]

Attest:

DONALD J. QUIGG

Attesting Officer    Commissioner of Patents and Trademarks